United States Patent [19]

Cleary

[11] Patent Number: 4,911,916

[45] Date of Patent: Mar. 27, 1990

[54] DIFFUSION MATRIX FOR TRANSDERMAL DRUG ADMINISTRATION AND TRANSDERMAL DRUG DELIVERY DEVICES INCLUDING SAME

[75] Inventor: Gary W. Cleary, San Mateo, Calif.

[73] Assignee: Cygnus Research Corporation, Redwood City, Calif.

[21] Appl. No.: 179,561

[22] Filed: Apr. 8, 1988

[30] Foreign Application Priority Data

Dec. 14, 1987 [AU] Australia ............................ 82499 87
Dec. 17, 1987 [EP] European Pat. Off. ......... 873113088
Dec. 22, 1987 [CA] Canada .................................. 555142

[51] Int. Cl.⁴ .............................................. A61F 13/00
[52] U.S. Cl. .................................. 424/449; 424/447; 424/448
[58] Field of Search ...................... 424/449, 447, 448

[56] References Cited

U.S. PATENT DOCUMENTS

| | | | |
|---|---|---|---|
| 3,426,754 | 2/1969 | Bierenbaum et al. | 128/156 |
| 3,486,968 | 12/1969 | Mater | 128/156 |
| 3,645,835 | 2/1972 | Hodgson | 128/156 |
| 3,685,734 | 8/1972 | Paciorek et al. | 424/443 |
| 3,699,963 | 10/1972 | Zaffaroni | 424/423 |
| 3,849,238 | 11/1974 | Gould et al. | 604/304 |
| 4,286,592 | 9/1981 | Chandrasekaran | 128/156 |
| 4,367,732 | 1/1983 | Paulsen et al. | 604/307 |
| 4,379,454 | 4/1983 | Campbell et al. | 128/156 |
| 4,438,139 | 3/1981 | Keith et al. | 424/78 |
| 4,452,845 | 6/1984 | Lloyd et al. | 128/156 |
| 4,460,371 | 7/1984 | Abber | 604/897 |
| 4,460,372 | 7/1984 | Campbell et al. | 604/897 |
| 4,510,197 | 4/1985 | Shah | 128/156 |
| 4,559,054 | 12/1985 | Bruck | 424/449 |
| 4,568,343 | 2/1986 | Leeper et al. | 604/896 |
| 4,573,995 | 3/1986 | Chen et al. | 604/896 |
| 4,588,580 | 5/1986 | Gale et al. | 424/449 |
| 4,600,001 | 7/1986 | Gilman | 604/304 |
| 4,638,797 | 1/1987 | Merrill et al. | 128/156 |
| 4,645,502 | 2/1987 | Gale et al. | 604/896 |
| 4,649,075 | 3/1987 | Jost | 424/449 |

FOREIGN PATENT DOCUMENTS 0196769 10/1988 European Pat. Off. .

OTHER PUBLICATIONS

A. S. Michaels, S. K. Chandrasekaran and J. E. Shaw—Drug Permeation Through Human Skin: Theory and *in Vitro* Experimental Measurement.

Y. W. Chien—Novel Drug Delivery Systems—Fundamentals, Development—Concepts, Biomedical Assessments.

*Primary Examiner*—Thurman K. Page
*Assistant Examiner*—P. L. Prater
*Attorney, Agent, or Firm*—Irell & Manella

[57] ABSTRACT

A solid state, resilient laminated composite for administering a drug transdermally consisting of a top layer of a resilient elastomer; a middle diffusion matrix layer composed of a polyurethane macroporous foam framework in whose pores are embedded a viscoelastic blend of a medical grade polysiloxane adhesive, drug, and optionally a percutaneous absorption enhancer, and a basal surface layer of the medical grade polysiloxane adhesive.

30 Claims, 1 Drawing Sheet

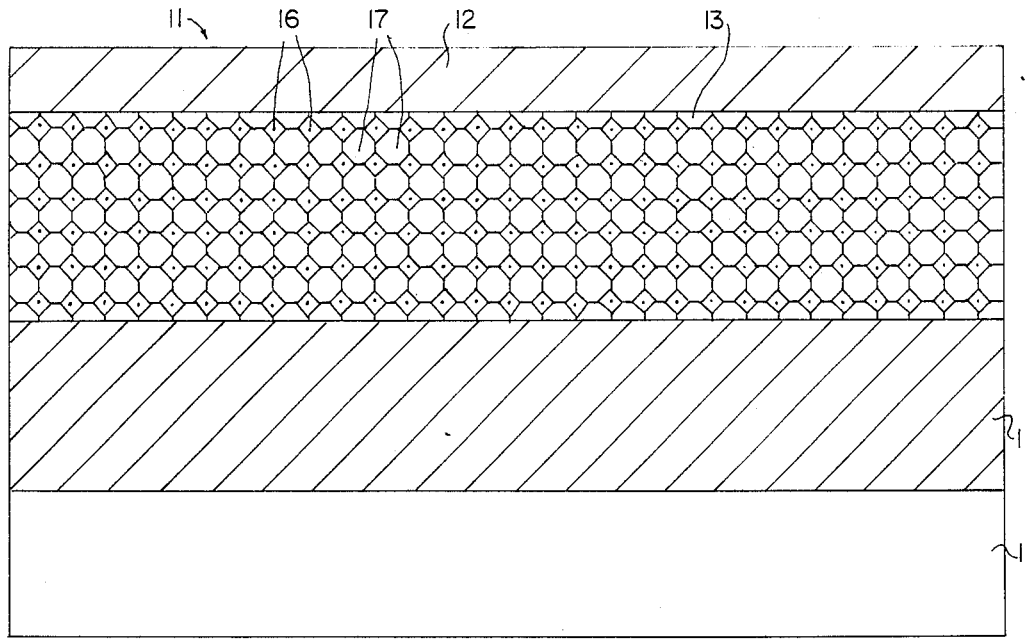

DIFFUSION MATRIX FOR TRANSDERMAL DRUG ADMINISTRATION AND TRANSDERMAL DRUG DELIVERY DEVICES INCLUDING SAME

CROSS-REFERENCE TO RELATED APPLICATIONS

This application is a continuation-in-part of U.S. patent application Ser. No. 945,389, filed Dec. 22, 1986 now abandoned.

TECHNICAL FIELD

This invention is in the field of transdermal drug delivery. More particularly it relates to: a diffusion matrix that serves as a drug reservoir in a transdermal drug delivery device; transdermal drug delivery devices that employ the diffusion matrix; transdermal drug delivery devices which include a pressure sensitive adhesive layer that contacts and adheres to the skin when the device is in use and means for replenishing the pressure sensitive adhesive in the layer so that the device may be repositioned or replaced on the skin without loss of adhesiveness.

BACKGROUND OF THE INVENTION

A variety of devices have been proposed or used for administering drugs transdermally. These devices are generally in the form of a bandage or skin patch that includes a reservoir that contains the drug and a pressure sensitive adhesive component by which the device is attached to the skin. Depending upon the inherent permeability of the skin to a particular drug, the device may also include means for coadministering a percutaneous absorption enhancer or an element, such as a membrane interposed between the reservoir and the skin, that regulates the rate at which the drug or the percutaneous absorption enhancer is administered to the skin.

Release of drug from the transdermal drug delivery device's reservoir typically occurs via diffusion. In such instances, the reservoir is often called a "diffusion matrix". These matrices are composed of a combination of drug-permeable polymer and drug in which the drug is typically dispersed in or encapsulated by the polymer.

The present invention involves a diffusion matrix that uses a reticulated macroporous polymeric foam as a framework for holding a viscoelastic drug-polymer mixture. Porous or foamed elements have been employed in transdermal drug delivery devices in the past but not in the same manner as in the present invention. In particular U.S. Pat. No. 3,797,494 describes the use of a microporous polymer that forms either the drug reservoir matrix or a membrane interposed between a drug reservoir layer and an adhesive layer. The pores of the material are filled with drug permeable liquid and the porous structure of the material is such that its porosity and tortuosity significantly affect the flux of drug through the liquid-filled material. U.S. Pat. No. 4,605,548 describes a transdermal drug delivery device that includes a porous membrane whose pores are filled with a drug-containing liquid that is held in the pores by capillary pressure. Japanese Patent Publication No. J57139011-A describes a matrix consisting of a water swellable porous membrane whose pores are filled with a drug-containing liquid. Finally, several Japanese Patent Publications (see Nos. J58096016-A, J570009714-A, and J5706413-A) describe the use of porous or foam layers as backing or support members in transdermal drug delivery devices. In each instance, the drug is contained in another element, typically in the adhesive layer that contacts the skin.

One shortcoming of prior transdermal drug delivery devices is that when they are removed from the skin the pressure sensitive adhesive tends to remain on the skin rather than staying part of the device. Thus, once removed from the skin, these prior devices would not adhere well to the same site or another site on the skin. This made it impossible or impractical to remove the device for bathing or other reasons. One aspect of the present invention is a transdermal drug delivery device that includes means for restoring the adhesiveness of the basal surface of the device after it has been removed from the skin. Applicant knows of no prior device that has such means.

DISCLOSURE OF THE INVENTION

One aspect of the invention is a diffusion matrix for use as a reservoir for a drug in a transdermal drug delivery device comprising a viscoelastic body of:
(a) a reticulated polymeric foam framework;
(b) a visoelastic drug-permeable hydrophobic polymer embedded in the pores of the foam;
(c) a drug dispersed in and at least partly dissolved in the hydrophobic polymer; and optionally
(d) an agent dispersed in and at least partly dissolved in the hydrophobic polymer that enhances the solubility of the drug in the polymer and/or is a percutaneous absorption enhancer that increases the permeability of skin to the drug.

Another aspect of the invention is a transdermal drug delivery device in the form of a laminated composite comprising:
(a) an optional backing layer that forms the top surface of the composite;
(b) a second layer consisting of the above-described drug diffusion matrix; and
(c) a third layer comprising a pharmaceutically acceptable pressure sensitive adhesive, one face of which defines the basal surface of the body and contacts and adheres to the skin when the device is in use, said third layer providing no rate controlling barrier to diffusion of components of the second layer from the second layer to the skin. Prior to use the device will also typically include a fourth release liner layer that covers the basal surface of the third layer. The release liner is removed from the device to expose the adhesive face of the third layer so that the device may be adhered to the skin.

In embodiments which involve a steroidal drug, such as estradiol, an opioid such as fentanyl or fentanyl analog, or other drug that requires the skin to be hydrated in order that it permeate through the skin at suitable rates, it may be necessary that the device be a sufficient barrier to water vapor transmission to cause the area of skin to become hydrated and thus more permeable to the drug.

Another aspect of the invention is the use of the same material as the hydrophobic polymer of the diffusion matrix and as the pressure sensitive adhesive in the above described transdermal drug delivery device.

Still another aspect of the invention is a device for administering a drug to a predetermined area of unbroken skin comprising a laminated composite that includes a diffusion matrix layer that contains the drug and a layer of a pressure sensitive adhesive which defines the basal surface of the composite and contacts and adheres to the skin when the device is in use, wherein the diffusion matrix layer contains a sufficient amount of the pressure sensitive adhesive to provide a means for replenishing the pressure sensitive adhesive in the pressure sensitive adhesive layer by mechanical flow of pressure sensitive adhesive from the diffusion matrix, whereby the device may be replaced or repositioned on the skin without significant loss of adhesiveness.

BRIEF DESCRIPTION OF THE DRAWING

The drawing shows a partly schematic, enlarged sectional view of a transdermal drug delivery device of the invention

MODES FOR CARRYING OUT THE INVENTION

The drawing shows a device, generally designated 11, that is designed specifically for administering a drug, for instance, estradiol, transdermally at therapeutically effective rates. Device 11 is in the form of a four-layer laminated composite that is adapted to be adhered to a predetermined area of unbroken skin. The four layers of the device are: a top backing or "outer skin" layer 12; a diffusion matrix layer 13; a pressure sensitive adhesive layer 14; and a release liner layer 15.

Backing layer 12 functions as the primary structural element of the device and provides the device with much of its resiliency, flexibility, suitable drape, and, where necessary, depending upon the nature of the drug, occlusivity. It also serves as a protective covering to prevent drug/enhancer from being transmitted from the device via the top surface of the diffusion matrix. The use of a such a backing layer is optional. When it is absent, other means must be used to provide the device with the requisite structural integrity. For instance, a structural element might be positioned elsewhere in the composite or materials that provide the desired mechanical properties might be used in the construction of the diffusion matrix. Backing 12 may also be used to impart the device with a desirable or necessary degree of occlusivity which in turn causes the area of skin on which the device is placed to become hydrated. In such a role, a layer is selected that has a level of water vapor transmissibility that makes the device occlusive to the degree required to cause the area of skin to be hydrated. In such instances it is preferable that the device provide at least about 90% hydration, more preferably at least about 95% hydration of the skin, as measured by a dielectric hydration probe available from Dr. Howard Maibach, U.C.S.F., San Francisco, Calif. Such occlusivity is desirable when drugs such as estradiol or fentanyl are being administered. If the drug being administered is such that skin hydration is not necessary or desirable, it is preferably to use layers that provide a composite that is "breathable", i.e., transmits water vapor from the skin to the atmosphere. Such breathability contributes to the nonocclusive nature of the composite and lessens the likelihood that the area of skin on which the composite is worn will become irritated. In nonocclusive embodiments of the device, the water vapor transmission rate (WVTR) of the laminated composite is typically in the range of 11-18 g/m$^2$-hr (as measured using an Evaporimeter at 20° C., 60% relative humidity).

Backing 12 is preferably made of a sheet or film of a resilient elastomer about 10 to about 75 microns thick. The resiliency of layer 12 permits the device to mimic the resiliency of the skin and be worn comfortably on areas of skin, such as at joints or other points of flexure, that are normally subjected to mechanical strain with little or no likelihood of the device disengaging from the skin due to differences in the flexibility or resiliency of the skin and the device. Examples of polymers that are useful for making layer 12 are polyether block amide copolymers (e.g., PEBAX copolymers), polyethylene methyl methacrylate block copolymers (EMA) such as NUKRELL polymers, polyurethanes such as PELLATHANE or ESTANE polymers, silicon elastomers, and polyester block copolymers that are composed of hard and soft segments (e.g., HYTREL polymers).

The diffusion matrix layer 13 functions as a reservoir for drug, percutaneous absorption enhancer and, optionally, pressure sensitive adhesive. The framework of the matrix is a reticulated macroporous polymer foam 16. The term "reticulated" intends a substantially (50% or more) open network. Preferably the network is essentially completely (90% or greater) open pores. The pore rating of the reticulated foam will normally be in the range of about 10 to 40 pores per linear centimeter and the density (unfilled) will typically be in the range of about 0.01 to 0.5 g/cm$^3$. Since the foam is macroporous rather than microporous, its porous structure does not affect significantly the flux of drug through the filled foam. Examples of suitable polymers from which the reticulated polymer foam framework may be made are polyurethanes and polyethylene. The pores of the foam are wholly or partly filled, preferably partly filled, with a viscoelastic hydrophobic drug-permeably polymer 17 that serves as a carrier for the drug and, when present, the percutaneous absorption enhancer. The term "partly filled" denotes conditions in which the surface of the pores is merely coated with the hydrophobic polymer and/or some pores are totally filled, while others either contain no hydrophobic polymer or are partly filled. In terms of weight ratios, the weight ratio of hydrophobic polymer (including drug and, when present, enhancer) to foam framework will usually be in the range of 1:1 to 10:1. It is estimated that at such weight ratios about one tenth to one third of the void volume of the foam will be filled with the hydrophobic polymer mixture. In its partly filled state the diffusion matrix layer is itself flexible, resilient, and compressible. Its compressiblity enables the diffusion matrix to absorb mechanical forces generated by skin movement.

In device 11 the hydrophobic polymer may optionally also be a medical grade pressure sensitive adhesive. In such instances, the polymer functions both as a carrier for the active ingredients of the device as well as a source of reserve pressure sensitive adhesive to replenish, if necessary, the adhesive that forms layer 14. In this regard since layer 13 is compressible, it may be compressed to force the hydrophobic polymer mixture from the pores to the basal surface of the device. The adhesive properties of the hydrophobic polymer may also provide the means by which backing layer 12 is affixed to the top surface of the diffusion matrix.

The hydrophobicity of polymer 17 renders the device water-resistant and prevents liquid water from being absorbed by the device and affecting its functionality or wearability. The diffusion coefficient of the polymer relative to the drug and the solubility of the drug in the polymer are such that the polymer is permeable to the drug. Polymers having diffusion coefficients (D) greater than about $10^{-14}$ cm$^2$/sec, usually in the range of $10^{-8}$ to $10^{-12}$ cm$^2$/sec (determined from desorption curves described by Baker R. W. and Lonsdale, H. K., *Controlled Release: Mechanism and Rates* in *Advances in Experimental Medicine and Biology,* Vol. 47, Tanquary, A. C. and Lacey, R. E. Eds, Plenum Press, N.Y., 1974), and in which the solubility of the drug is greater than about 1 mg/ml, usually in the range of 1 to 50 mg/ml, are suitable. In embodiments of the device that include a percutaneous absorption enhancer, the hydrophobic polymer is also permeable to the enhancer. Examples of polymer types that have the required hydrophobicity and drug permeability and desirable adhesive characteristics are polyhsiloxanes (silicone polymers), hydrophobic polyacrylates, polyurethanes, plasticized ethylene-vinyl acetate copolymers and low molecular weight polyether block amide copolymers (PEBAX copolymers) and tacky rubbers such as polyisobutene. Polysiloxanes are preferred.

The term "drug" as used to describe the principal active ingredient of the device intends a biologically active compound or mixture of compounds that has a therapeutic, prophylactic or other beneficial pharmacological and/or physiological effect on the wearer of the device. Examples of types of drugs that may be used in the invention device are antiinflammatory drugs, analgesics, antiarthritic drugs, antispasmodics, antidepressants, antipsychotic drugs, tranquilizers, narcotic antagonists, antiparkinsonism agents, anticancer drugs, immunosuppression agents, antiviral agents, antibiotic agents, appetite suppressants, antiemetics, anticholinergics, antihistaminics, antimigraine agents, coronary, cerebral or peripheral vasodilators, hormonal agents, contraceptive agents, antithrombotic agents, diuretics, antihypertensive agents, cardiovascular drugs, opioids, and the like. The appropriate drugs of such types are capable of permeating through the skin either inherently or by virtue of treatment of the skin with a percutaneous absorption enhancer. Because the size of the device is limited for patient acceptance reasons, the preferred drugs are those that are effective at low concentration in the blood stream. Examples of specific drugs are estradiol, progesterone, demegestone, promegestrone, testosterone and their esters, nitro-compounds such as nitroglycerine and isosorbide nitrates, nicotine, chlorpheniramine, terfenadine, triprolidine, hydrocortisone, oxicam derivatives such as piroxicam, mucopolysaccharidases such as thiomucase, buprenorphine, fentanyl and fentanyl derivatives or analogs, naloxone, codeine, dihydroergotamine, pizotiline, salbutamol, terbutaline, prostaglandins such as misoprostol and enprostil, omeprazole, imipramine, benzamides such as metoclopramine, scopolamine, peptides such as growth releasing factor and somatostatin, clonidine, dihydropyridines such as nifedipine, verapamil, ephedrine, propanolol, metoprolol, sipronolactone, thiazides such as hydrochlorothiazide, flunarizine, sydononimines such as molsidomine, sulfated polysaccharides such as heparin fractions and the salts of such compounds with pharmaceutically acceptable acids or bases, as the case may be. The drug may be either wholly or partly dissolved in the hydrophobic polymer. The loading of drug in the polymer will depend on the intended lifetime of the device and will usually be in the range of about 1% to 20% by weight, based on the total weight of the mixture filling the pores of the foam.

Since the inherent permeability of the skin to some drugs such as estradiol is too low to permit therapeutic levels of such drugs to pass through a reasonably sized area of unbroken skin, it is necessary to coadminister a percutaneous adsorption enhancer with such drugs. Accordingly, a percutaneous adsorption enhancer is present in the hydrophobic polymer along with such drug. In addition to affecting the permeability of the skin to the drug, the enhancer may also increase the solubility of drug in the hydrophobic polymer and thereby increase the permeability of the polymer to the drug.

Applicant has found that fatty acid esters (monoester, diester or mixtures thereof) or fatty alcohol ethers (monoether, diether, or mixtures thereof) of $C_2$ to $C_4$ alkanediols, where each fatty acid/alcohol portion of the ester/ether is of about 8 to 22 carbon atoms and is straight or branched chain, preferably straight chain, is saturated or has 1 to 3 sites of olefinic unsaturation and has 0 to 2 hydroxyl groups, are phase compatible with the preferred type of hydrophobic polymer, increase the solubility of estradiol in such polymer, and enhance the permeability of skin to estradiol when coadministered to the skin. Monoesters and monoethers of straight chain alkanediols whose hydroxyl groups are on terminal carbon atoms are preferred. Monoesters of propylene glycol, especially propylene glycol monolaurate (PGML), are particularly preferred. Examples of such esters and ethers are ethylene glycol octanoate, ethylene glycol monolaurate, ethylene glycol dilaurate, ethylene glycol monoeicosanate, ethylene glycol monostearate, ethylene glycol dioleate, ethylene glycol monolinoleate, propylene glycol monolaurate, propylene glycol dilaurate, propylene glycol monopalmitate, propylene glycol monostearate, propylene glycol monooleate, butylene glycol monodecanoate, butylene glycol monolaurate, butylene glycol monopalmitate, butylene glycol monostearate, 2-hydroxyethyloctyl ether, 2-hydroxyethyllauryl ether, 2-hydroxyethylhexadecyl ether, 2-hydroxyethyleicosyl ether, 3-hydroxypropyllauryl ether, 3-hydroxypropyltetradecyl ether, 3-hydroxyethyloctadecyl ether, 4-hydroxybutyldocecyl ether, and 4-hydroxybutyloctadecyl ether. The enhancer is dispersed in the hydrophobic polymer in amounts that are sufficient to provide functional amounts of enhancer over the intended lifetime of the device. In the case of device 11, the loading of enhancer in the hydrophobic polymer will usually be in the range of 2% to 20% by weight, based on the mixture filling the pores of the foam.

It will be appreciated that other percutaneous absorption enhancers, such as those taught in U.S. Pat. Nos. 4,379,454 and 4,568,343, may be coadministered with estradiol to enhance the permeability of the skin to estradiol. In this regard, the enhancer should be phase compatible (i.e., it should not bloom) with the hydrophobic polymer.

Of course, when the invention device is used to administer drugs other than estradiol to which the permeability of the skin is inherently too low to pass therapeutic amounts, the above described esters or ethers or known enhancers (see, for instance, the above mentioned patents and the references cited in the mentioned patents) will be included in the device and coadministered with the drug. Correlatively, when the device is used to administer a drug to which the permeability of the skin is inherently sufficient to pass therapeutic amounts, it is not necessary to coadminister an enhancer. Thus, in a general terms, the inclusion of an enhancer in the device is optional depending upon the particular drug that is being administered.

The thickness of layer 13 will depend upon the intended lifetime of the device. Thicker layers (and hence more drug and, when present, enhancer) will be used to increase the lifetime. In the case of estradiol, the device will typically be designed to have an effective lifetime of about 3 to 14 days; whereas with fentanyl the effective lifetime will be about 1 to 7 days. In such embodiments, the thickness of the diffusion matrix layer will normally be in the range of about 10 to 2500 microns, preferably 500 to 1200 microns.

Device 11 does not include means for controlling the rate at which either the drug or the enhancer is administered to the skin. Instead, in the case of an estradiol or fentanyl device employing PGML as enhancer, estradiol/fentanyl is presented to the skin at rates in excess of that which the treated area of the skin is able to absorb, while PGML is presented to the skin in quantities sufficient to allow necessary skin interaction. The system does not control either the rate of administration of estradiol/fentanyl or PGML. Increasing the concentrations and thermodynamic activities of the PGML in the system does not increase estradiol/fentanyl flux appreciably beyond a limiting PGML concentration in the range of 6% to 10% in the hydrophobic polymer. At PGML concentrations equal to or above this level, estradiol/fentanyl skin permeation becomes essentially constant and independent of PGML driving force in the system or drug loading above the limiting level necessary to provide equilibrium saturation in all layers and components of the composite.

It will be appreciated, however, that depending upon the particular drug (and enhancer when one is needed) that is being administered, that it may be necessary or desirable to include an element in the device that will control the release rate of the drug and/or the enhancer. Such elements are known in the art. The most common is a polymer membrane having appropriate drug/enhancer permeability properties interposed between the diffusion matrix layer and the pressure sensitive adhesive layer.

It should be understood that the concentrations of drug/enhancer in the layers that are specified above are as of the time of manufacture and that these concentrations may change as concentrations reach equilibrium in accordance with solubility parameters.

The pressure sensitive adhesive layer 14 is composed of a medical grade adhesive composition. In embodiments of the device in which a pressure sensitive adhesive is used as the hydrophobic polymer of the diffusion matrix, it is preferable to use the same hydrophobic polymer to form layer 14. In such instances the porous nature of the diffusion matrix permits hydrophobic polymer (adhesive) to flow from the matrix and replenish that which may be lost from layer 14 when the device is replaced or repositioned on the skin. The thickness of layer 14 will normally be in the range of 25 to 100 microns, preferably 50 to 75 microns. Depending upon the particular drug, enhancer, and pressure sensitive adhesive used, it may be desirable to pre-load layer 14 with drug and/or enhancer to prevent of reduce migration of drug/enhancer from the diffusion matrix before the device is used. As is understood in the art, if such pre-loading is not employed, the drug/enhancer will migrate into layer 14 until concentration equilibrium is reached. Pre-loading is preferred to provide stable drug/enhancer release profiles for quality control monitoring. The composition and thickness of layer 14 are such that layer 14 is not a rate controlling barrier to diffusion of drug/enhancer from layer 13 to the skin.

Prior to use device 11 includes a release liner layer 15. Just prior to use this layer is stripped off the device to expose layer 14. This material will normally be made from a drug/enhancer impermeable material that is inherently strippable or rendered so by techniques such as silicone or fluorocarbon treatment.

The rate at which drug/enhancer is/are administered from the device to circulation will depend upon the particular drug/enhancer involved and the basal surface area (the area contacting the skin) of the device. In the case of estradiol used to treat postmenopausal symptoms or osteoporosis, the device should provide sufficient supplemental estradiol (in addition to base level in the patient) to yield steady state plasma levels of estradiol in the range of about 20 to 80 pg/ml. In the case of fentanyl used for the relief of post-operative or chronic pain, the device should provide adequate fentanyl to yield steady state plasma levels of fentanyl in the range of about 2 to 10 mg/ml. In vitro tests such as that described in *Medical Device and Diagnostic Industry* (1985) 8:35–42 may be used to estimate the flux of drug through human cadaver skin from the devices of the invention. The flux of estradiol from device 11 will normally be in the range of 0.05 to 0.4 $\mu g/cm^2/hr$, more usually 0.1 to 0.2 $\mu g/cm^2/hr$. In the case of fentanyl, this will normally be in the range of 0.2 to 45 $\mu g/cm^2/hr$. The basal surface area of device 11 will usually be in the range of 2.5 to 40 $cm^2$.

Since device 11 has no fluid elements (i.e., it is a solid state device at normal wearing temperatures, i.e. less than 40° C.), it is readily manufactured using conventional casting and laminating techniques. Commercially available films may be used for backing layer 12, the reticulated polymer foam framework 16 of the diffusion matrix, and release liner layer 15. The mixture of hydrophobic polymer, drug and, when required, enhancer may be blended using suitable solvents and conventional blending equipment and cast into the pores of the reticulated polymer foam. Upon evaporation of the solvent, the embedded mixture solidifies. The resulting diffusion matrix may then be laminated to the backing layer. The pressure sensitive adhesive layer may be cast in solution onto the release liner to form an adhesive-release liner subassembly. That subassembly is then laminated to the backing-diffusion matrix subassembly. Lamination may be accomplished by thermal bonding, solvent bonding or through use of adhesives as is known in the art. Devices of desired basal surface area may be punched or otherwise formed from the thus assembled laminated composite.

The following examples further illustrate various aspects of the invention. These examples are not intended to limit the invention in any manner. The commercial PGML used in the examples was found to contain substantial amounts, i.e., up to 40% by weight of the dilaurate. Commerical PGML may also contain minor amounts (e.g., up to 10% to 15% by weight) of other ingredients such as methyl laurate and/or propylene glycol. Thus, as used herein, the term "PGML" is intended to include commercial PGML as well as purified PGML.

EXAMPLE 1

A drug-polymer mixture containing 5% w/w estradiol (E2), 10% commercial propylene glycol monolaurate (PGML) and 85% polydimethylsiloxane (Dow Corning 355 Medical Grade Adhesive) was dissolved into a 50% final solid content solution with trichlorotrifluoroethane (freon). The resulting solution was then cast into the open pores of a 1200 micron thick preformed polyurethane foam (Scotfoam, pore rating 30 pores/cm) using a 750 micron gap Gardner knife, a 25 micron thick polyurethane backing film (Medifilm 426, Schoeller, Inc.) having been previously flame sealed onto the opposite surface of the foam structure. The solvent was evaporated leaving a resultant foam structure containing approximately 20 mg/cm$^2$ E2/PGML/polydimethylsiloxane per 7.5 mg/cm$^2$ polyurethane foam (precoating foam weight).

A contact adhesive containing 2% w/w E2, 10% PGML and 88% polydimethylsiloxane (Dow Corning 355) was dissolved to a 50% final solids content solution with freon. The contact adhesive solution was then cast using a 100 micron gap Gardner knife onto a fluorocarbon-coated polyester film (3M, 1022). The solvent was evaporated leaving a resultant 50 micron thick contact adhesive coating.

The polyurethane foam/E2/PGML/siloxane drug reservoir composite was laminated to the 50 micron thick contact adhesive layer such that the fluorinated polyester film served as a peelable protective strip. The resultant laminate was die cut to fit diffusion cells and backed with an occlusive layer of aluminum foil and E2 flux across human cadaver skin was determined at 32° C. by the procedures described in *Medical Device and Diagnostic Industry* (1985) 8:35–42. The steady state E2 flux was determined to be ~0.18 $\mu$g/cm$^2$ hr.

The laminated composite was translucent and resilient which allows the entire composite to stretch with the stretching of skin. Young's modulus, % elongation and tensile strength were determined to be 14.07 kg/cm$^2$, 425% and 7.81 kg/cm$^2$, respectively using an Instron model 1011 with a crosshead speed of 30 cm/min. In addition, it was repeatedly repositioned on human skin without any apparent loss of adhesiveness.

EXAMPLE 2

A laminated composite was made and tested as in Example 1 using 2% E2, 6% PGML and 92% polysiloxane (Dow Corning 355) for the drug-polymer reservoir and 1.3% E2, 6% PGML and 92.7% polysiloxane (Down Corning 355) for the contact adhesive. The steady state estradiol flux across human cadaver skin was determined to be ~0.12 $\mu$g/cm$^2$ hr while the Young's modulus, % elongation and tensile strength were determined to be 11.96 kg/cm$^2$, 430% and 9.36 kg/cm$^2$, respectively. These values are substantially the same as Example 1.

EXAMPLE 3

A laminated composite was made and tested above using a drug-polymer reservoir consisting of 4% E2, 10% PGML and 86% polydimethylsiloxane (Dow Corning X7-2909) and a contact adhesive consisting of 10% PGML and 90% polydimethylsiloxane. The steady state skin flux was determined to be ~0.12 $\mu$g/cm$^2$ hr which is substantially the same as from the composite of Example 1.

EXAMPLE 4

A laminated composite was made and tested as above except that the polydimethylsiloxane polymer was substituted with polymethylphenylsiloxane (marketed under the mark Flexcon). Estradiol-steady state flux across human skin was substantially the same as from the composite of Example 1.

EXAMPLE 5

Laminated composites were made as in Example 2 using Dow Corning polydimethylsiloxane XT-2675 with similar results.

EXAMPLE 6

Laminated composites were made as in Examples 1 and 2 using other types of Medifilm backing (Medifilm 810 827 both polyether block amide copolymers) with similar results.

EXAMPLE 7

A laminated composite is made as in Example 1 substituting progesterone for estradiol in both drug-polymer reservoir and contact adhesive.

EXAMPLE 8

A laminated composite is made as in Example 1 substituting demegestone for estradiol in both drug-polymer reservoir and contact adhesive.

EXAMPLE 9

A laminated composite is made as in Example 1 substituting promegestrone for estradiol in both drug-polymer reservoir and contact adhesive.

EXAMPLES 10, 11, and 12

Laminated composites are made as in Example 1 incorporating 2% E2, 2% either progesterone, demegestone, or promegestrone, 10% PGML and 86% polydimethylsiloxane into the drug-polymer reservoir and 1.3% E2, 1.3% either progesterone, demegestone, or promegestrone, 10% PGML and 87.4% polydimethylsiloxane as the contact adhesive.

Modifications of the above described modes for carrying out the invention that are obvious to those of ordinary skill in the field of transdermal drug delivery devices and related fields are intended to be within the scope of the following claims.

I claim:

1. A diffusion matrix for use as a reservoir for a drug in a transdermal drug delivery device comprising a viscoelastic body of:
   (a) a reticulated macroporous polymeric foam framework;
   (b) a viscoelastic drug-permeable hydrophobic polymer embedded in the pores of the foam; and
   (c) a drug dispersed in and at least partly dissolved in the hydrophobic polymer that is capable of permeating through unbroken skin, the loading of drug in the polymer being in the range of about 1% to 20% by weight.

2. The diffusion matrix of claim 1 including:
   an agent dispersed in and at least partly dissolved in the hydrophobic polymer that enhances the solubility of the drug in the polymer and/or is a percutaneous absorption enhancer that increases the permeability of the skin to the drug.

3. The diffusion matrix of claim 1 wherein the drug is estradiol, progesterone, piroxicam, fentanyl, a fentanyl analog, dihydroergotamine, salbutamol, nifedipine, spironolactone, demegestone, promegestrone, hydrochlorothiazide, nicotine, chlorpheniramene or triprolidine.

4. The diffusion matrix of claim 1 wherein the reticulated polymeric foam framework is made of a polyurethane or polyethylene.

5. The diffusion matrix of claim 1 wherein the weight ratio of (b) and (c) combined to (a) is in the range of about 1:1 to 10:1.

6. The diffusion matrix of claim 1 wherein the pore rating of the reticulated polymeric foam framework is about 10 to 40 pores per linear centimeter and the density of the reticulated polymeric foam framework in the range of about 0.01 and 0.5 g/cm$^3$.

7. The diffusion matrix of claim 1 wherein the hydrophobic polymer is a pharmaceutically acceptable pressure sensitive adhesive.

8. The diffusion matrix of claim 7 wherein the hydrophobic polymer is a polysiloxane, a polyacrylate, a polyurethane, a plasticized ethylenevinyl acetate copolymer, a polyether blockamide copolymer or a tacky rubber.

9. The diffusion matrix of claim 7 wherein the hydrophobic polymer is a polydimethylsiloxane or a polymethylphenylsiloxane.

10. The diffusion matrix of claim 1 wherein the diffusion coefficient of the polymer to the drug is greater than about $10^{-14}$ cm$^2$/sec and the solubility of the drug in the hydrophobic polymer is greater than about 1 mg/ml.

11. The diffusion matrix of claim 1 wherein the diffusion coefficient of the polymer to the drug is in the range of $10^{-8}$ to $10^{-12}$ cm$^2$/sec and the solubility of the drug in the hydrophobic polymer is in the range of 1 to 50 mg/ml.

12. The diffusion matrix of claim 2 wherein the agent is a fatty acid ester or fatty alcohol ether of a $C_2$ to $C_4$ alkanediol where each fatty acid or fatty alcohol portion of the ester or ether is of about 8 to 22 carbon atoms.

13. The diffusion matrix of claim 2 wherein the agent is a fatty acid monoester of fatty alcohol monoether of a $C_2$ to $C_4$ alkanediol.

14. The diffusion matrix of claim 2 wherein the drug is estradiol or fentanyl and the agent is propylene glycol monolaurate.

15. The diffusion matrix of claim 14 wherein the reticulated macroporous polymeric foam is made of a polyurethane having a pore rating of about 10 to 40 pores per linear centimeter and a density in the range of about 0.01 to 0.5 g/cm$^3$, the hydrophobic polymer is a polydimethylsiloxane, the weight ratio of the polydimethylsiloxane, estradiol/fentanyl and propylene glycol monolaurate combined to the polyurethane is in the range of 1:1 and 10:1, and the loading of propylene glycol monolaurate in the polydimethylsiloxane is 2% to 20% by weight based on the weight of material embedded in the pores of the foam.

16. The diffusion matrix of claim 15 wherein the body is in the form of a thin film about 10 to 2500 microns thick.

17. A transdermal drug delivery device for administering a drug to a predetermined area of unbroken skin, said device being a resilient laminated composite comprising:

(a) the drug diffusion matrix of claim 1, and (b) a layer of a pharmaceutically acceptable pressure sensitive adhesive, one face of which defines the basal surface of the body and contacts and adheres to the skin when the device is in use, said layer providing no rate controlling barrier to diffusion of components of the diffusion matrix from the diffusion matrix to the skin.

18. The device of claim 17 including:

a backing layer that forms the top surface of the composite.

19. The device of claim 18 including:

a release liner layer that covers said one face of the layer of pharmaceutically acceptable pressure sensitive adhesive and is adapted to be removed from the device prior to use to expose said one face of the layer of pharmaceutically acceptable pressure sensitive adhesive.

20. The device of claim 18 wherein the hydrophobic polymer and the pressure sensitive adhesive are the same material.

21. The device of claim 18 wherein the drug is estradiol, progesterone, piroxicam, fentanyl, a fentanyl analog, dihydroergotamine, salbutamol, nifedipine, spironolactone, hydrochlorothiazide, promegestrone, demegestone, nicotine, chlorpheniramine, or triprolidene.

22. A transdermal drug delivery device for administering a drug to a predetermined area of unbroken skin, said device being a resilient laminated composite comprising:

(a) the drug diffusion matrix of claim 2, and (b) a layer of a pharmaceutically acceptable pressure sensitive adhesive, one face of which defines the basal surface of the body and contacts and adheres to the skin when the device is in use, said layer providing no rate controlling barrier to diffusion of components of the diffusion matrix from the diffusion matrix to the skin.

23. The device of claim 22 including:

an occlusive backing layer that forms the top surface of the device.

24. The device of claim 23 including:

a release liner layer that covers said one face of the layer of pharmaceutically acceptable pressure sensitive adhesive and is adapted to be removed from the device prior to use to expose said one face of the layer of pharmaceutically acceptable pressure sensitive adhesive.

25. The device of claim 23 wherein the hydrophobic polymer and the pressure sensitive adhesive are the same material.

26. The device of claim 25 wherein the drug is estradiol or fentanyl, the pore rating of the polymeric foam is 10 to 40 pores per linear centimeter, the density of the polymeric foam is 0.01 to 0.5 g/cm$^3$, the weight ratio of the hydrophobic polymer, estradiol/fentanyl, and agent combined to the foam is 1:1 to 10:1, the hydrophobic polymer is a polysiloxane pressure sensitive adhesive, the hydrophobic polymer and the pressure sensitive adhesive of the pressure sensitive adhesive layer are the same material, the agent is a fatty acid ester or fatty alcohol ether of a $C_2$ to $C_4$ alkanediol where each fatty acid or fatty alcohol portion of the ether is of 8 to 22 carbon atoms and the loading of agent in the hydrophobic polymer is 2% to 20% based on the weight of the material embedded in the pores of the foam and the thickness of the diffusion matrix layer is about 10 to 2500 microns.

27. The device of claim 26 wherein the agent is a fatty acid monoester of propylene glycol.

28. The device of claim 26 wherein the agent is propylene glycol momolaurate.

29. The device of claim 28 wherein the pressure sensitive adhesive layer is preloaded with estradiol/fentanyl and propylene glycol momolaurate.

30. A transdermal drug delivery device for administering a drug to a predetermined area of unbroken skin comprising a laminated composite that includes a diffusion matrix layer that contains the drug and a layer of a viscoelastic pressure sensitive adhesive that defines the basal surface of the composite and contacts and adheres to the skin when the device is in use, wherein the diffusion matrix layer is in the form of a macroporous polymeric foam in whose pores are embedded a dispersion of the drug in the pressure sensitive adhesive and the diffusion matrix layer contains a sufficient amount of the pressure sensitive adhesive to provide a means for replenishing the pressure sensitive adhesive in the pressure sensitive adhesive layer by flow of pressure sensitive adhesive from the diffusion matrix to said basal surface, whereby the device may be replaced or repositioned on the skin without significant loss of adhesiveness.

* * * * *

UNITED STATES PATENT AND TRADEMARK OFFICE
CERTIFICATE OF CORRECTION

PATENT NO. : 4,911,916

DATED : March 27, 1990

INVENTOR(S) : Gary W. Cleary

It is certified that error appears in the above-identified patent and that said Letters Patent is hereby corrected as shown below:

On the title page, after Filed: April 8, 1988, please add:

--Related U.S. Application Data

Continuation-in-part of Ser. No. 06/945,389, December 22, 1986, abandoned.--

Signed and Sealed this

Sixth Day of October, 1992

Attest:

DOUGLAS B. COMER

Attesting Officer     Acting Commissioner of Patents and Trademarks